(12) United States Patent
Nishino et al.

(10) Patent No.: US 9,187,442 B2
(45) Date of Patent: Nov. 17, 2015

(54) METHOD FOR PRODUCING STEREOSELECTIVE EPOXYKETONE COMPOUND

(71) Applicant: NISSAN CHEMICAL INDUSTRIES, LTD., Chiyoda-ku (JP)

(72) Inventors: Yukihiro Nishino, Sanyo-Onoda (JP); Kazuya Wakui, Sanyo-Onoda (JP); Shota Murase, Sanyo-Onoda (JP); Yoshifumi Sakai, Sanyo-Onoda (JP)

(73) Assignee: Nissan Chemical Industies, Ltd., Chiyoda-ku (JP)

( * ) Notice: Subject to any disclaimer, the term of this patent is extended or adjusted under 35 U.S.C. 154(b) by 0 days.

(21) Appl. No.: 14/391,033

(22) PCT Filed: Jun. 27, 2013

(86) PCT No.: PCT/JP2013/068308
§ 371 (c)(1),
(2) Date: Oct. 7, 2014

(87) PCT Pub. No.: WO2014/003203
PCT Pub. Date: Jan. 3, 2014

(65) Prior Publication Data
US 2015/0126755 A1    May 7, 2015

Related U.S. Application Data

(60) Provisional application No. 61/735,196, filed on Dec. 10, 2012, provisional application No. 61/789,996, filed on Mar. 15, 2013.

(30) Foreign Application Priority Data

Jun. 29, 2012  (JP) .................................. 2012-146821
Feb. 14, 2013  (JP) .................................. 2013-026801

(51) Int. Cl.
*C07D 301/03* (2006.01)
*C07C 233/00* (2006.01)
(Continued)

(52) U.S. Cl.
CPC ............ *C07D 301/00* (2013.01); *C07C 213/00* (2013.01); *C07C 269/06* (2013.01); *C07D 301/19* (2013.01); *C07D 303/36* (2013.01)

(58) Field of Classification Search
CPC .. C07D 303/36; C07D 301/19; C07C 213/00; C07C 269/06
USPC ................................... 549/523; 564/152, 123
See application file for complete search history.

(56) References Cited

U.S. PATENT DOCUMENTS 8,609,654 B1    12/2013  Shenk et al.
2005/0256324 A1  11/2005  Laidig et al.
(Continued)

OTHER PUBLICATIONS

Benedetti et al , Versatile and Stereoselelctive Synthesis of Diamino diol Dipeptide Isosteres, Core Units of Pseudopeptide HIV Proteease Inhibitors, J. Org. Chem., 1997, 62, p. 9348-9353.*
(Continued)

OTHER PUBLICATIONS

*Primary Examiner* — T. Victor Oh
(74) *Attorney, Agent, or Firm* — Oblon, McClelland, Maier & Neustadt, L.L.P.

(57) ABSTRACT

A novel method for producing a stereoselective epoxyketone compound is provided. A method for producing an epoxyketone compound represented by the formula (1), as represented by the following scheme, whereby it is possible to obtain an epoxyketone derivative in good yield and at high selectivity and to provide an industrially useful production method and an intermediate thereof. wherein $R^1$ is a hydrogen atom, a linear, branched or cyclic alkyl group, an aromatic group which may have a substituent, or a heterocyclic group which may have a substituent, and $R^2$ is a protective group for an amino group. R is a hydrogen atom or a $C_{1-10}$ alkyl group, and R's may be the same or different, provided that at least one R is a $C_{1-10}$ alkyl group.

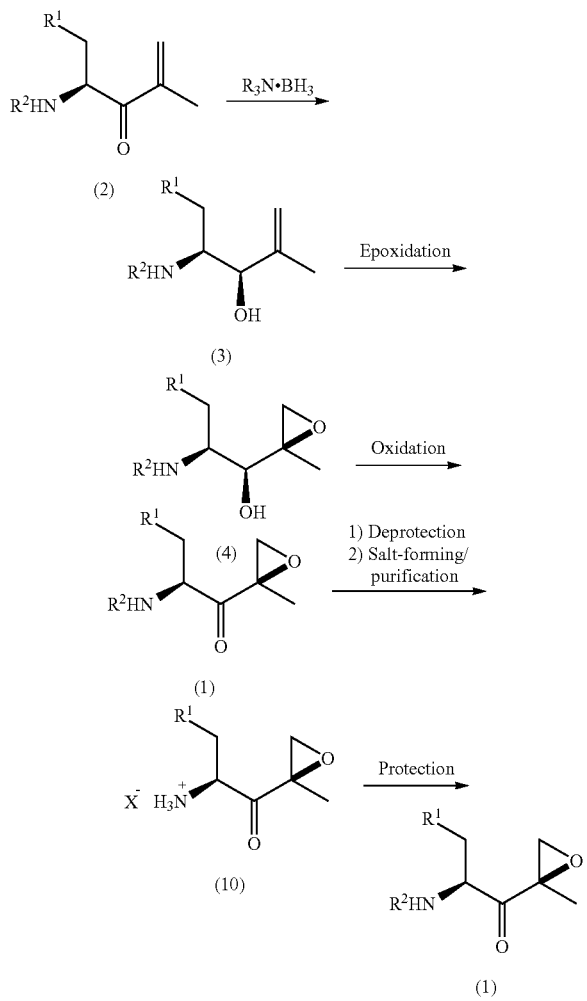

14 Claims, No Drawings

(51) Int. Cl.
- *C07D 301/00* (2006.01)
- *C07C 269/06* (2006.01)
- *C07D 301/19* (2006.01)
- *C07D 303/36* (2006.01)
- *C07C 213/00* (2006.01)

(56) References Cited

U.S. PATENT DOCUMENTS

| | | |
|---|---|---|
| 2007/0293465 A1 | 12/2007 | Shenk et al. |
| 2009/0105156 A1 | 4/2009 | Phiasivongsa et al. |
| 2010/0144648 A1 | 6/2010 | Shenk et al. |
| 2010/0144649 A1 | 6/2010 | Shenk et al. |
| 2012/0088762 A1 | 4/2012 | Shenk et al. |
| 2013/0035297 A1 | 2/2013 | Shenk et al. |
| 2013/0041008 A1 | 2/2013 | Shenk et al. |
| 2013/0053303 A1 | 2/2013 | Shenk et al. |
| 2013/0150289 A1 | 6/2013 | Phiasivongsa et al. |
| 2013/0150290 A1 | 6/2013 | Phiasivongsa et al. |

OTHER PUBLICATIONS

International Search Report issued Feb. 4, 2014, in PCT/JP13/068308, filed Jun. 27, 2013.

Written Opinion of the International Searching Authority issued Feb. 4, 2014, in PCT/JP13/068308, filed Jun. 27, 2013.

Zhou, Han-Jie, et al , "Design and Synthesis of an Orally Bioavailable and Selective Peptide Epoxyketone Proteasome Inhibitor (PR-047)", J. Med. Chem., vol. 52, No. 9, pp. 3028-3038, XP055086446, 2009.

Sin, N., et al., "Total Synthesis of The Potent Proteasome Inhibitor Epoxomicin: a Useful Tool for Understanding Proteasome Biology", Bioorganic & Medicinal Chemistry Letters, vol. 9, pp. 2283-2288, 1999.

\* cited by examiner

METHOD FOR PRODUCING STEREOSELECTIVE EPOXYKETONE COMPOUND

CROSS-REFERENCE TO RELATED APPLICATIONS

This application is a National Stage of PCT/JP2013/068308 filed on Jun. 27, 2013. This application is based upon and claims the benefit of priority to U.S. Provisional Application No. 61/735,196 filed on Dec. 10, 2012, and to U.S. Provisional Application No. 61/789,996 filed on Mar. 15, 2013, the entire contents of both of which are incorporated herein by reference.

TECHNICAL FIELD

The present invention relates to a method for producing an epoxyketone compound which is useful as an intermediate of medicine.

BACKGROUND ART

Epoxyketone derivatives represented by the structural formulae (1a) and (1b) (wherein PG is a protective group, Boc is a t-butyloxycarbonyl group and Cbz is a benzyloxycarbonyl group, and hereinafter, the same applies in this specification) are important compounds as raw materials for medicines, etc. (Non-patent Document 1 and Patent Document 3). Heretofore, as methods for their production, a production method of directly epoxidizing an α,β-unsaturated ketone (2a) (Non-patent Document 1) and a synthetic method of epoxidizing an allyl alcohol (3a) or (3b) obtainable by reducing an α,β-unsaturated ketone (2a) or (2b), followed by oxidation of an epoxy alcohol (4a) or (4b) (Patent Documents 1, 2 and 3), have been known.

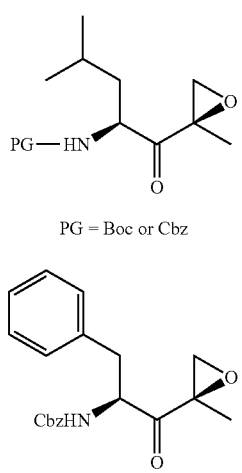

PG = Boc or Cbz

PRIOR ART DOCUMENTS

Patent Documents

Patent Document 1: US Patent Application Publication No. 2005/0256324A1
Patent Document 2: US Patent Application Publication No. 2009/0105156A1
Patent Document 3: US Patent Application Publication No. 2007/0293465A1

Non-Patent Documents

Non-patent Document 1: Bioorg. Med. Chem. Lett., (1999), 9, 2283

DISCLOSURE OF INVENTION

Technical Problem

In the epoxidation reaction of an α,β-unsaturated ketone (2a) disclosed in Non-patent Document 1, the stereoselectivity is low at a level of (1a):(1'a)=1.7:1, and, as such, the reaction cannot be regarded as a practical method.

(Non-Patent Document 1)

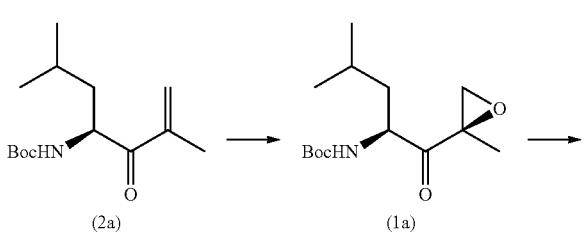

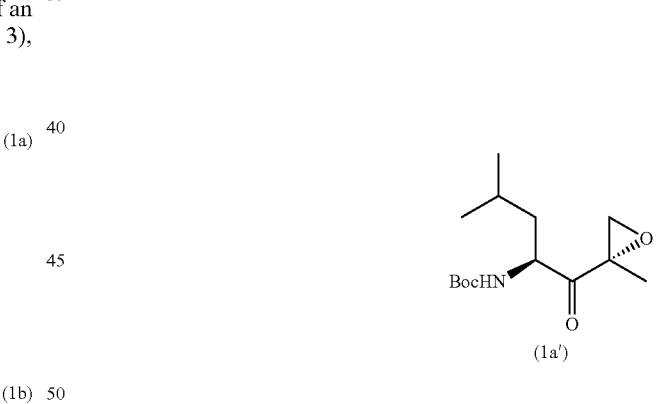

Whereas in the method via an allyl alcohol intermediate (3a) or (3b) as disclosed in Patent Documents 1, 2 and 3, it is possible to obtain an epoxy alcohol compound (4a) or (4b) stereoselectively from an allyl alcohol (3a) or (3b), but in Patent Document 1, when L-Selectride is used for reduction from an α,β-unsaturated ketone (2a) (PG=Cbz) to (3a), while the selectivity is high at a level of (3a):(3'a)=25:1, (5a) having a double bond reduced, is the main product, whereby the yield becomes low and such a method is not practical. When reduction is carried out by means of $CeCl_3/NaBH_4$, formation of (5a) as a byproduct can be avoided, but the selectivity will decrease to a level of (3a):(3'a)=9:1. According to the method disclosed in Patent Document 2, the selectivity when an α,β-unsaturated ketone (2a) (PG=Boc) is reduced by means of $CeCl_3/NaBH_4$, is at a level of (3a):(3'a)=4.5:1.

(Patent Documents 1 and 2)

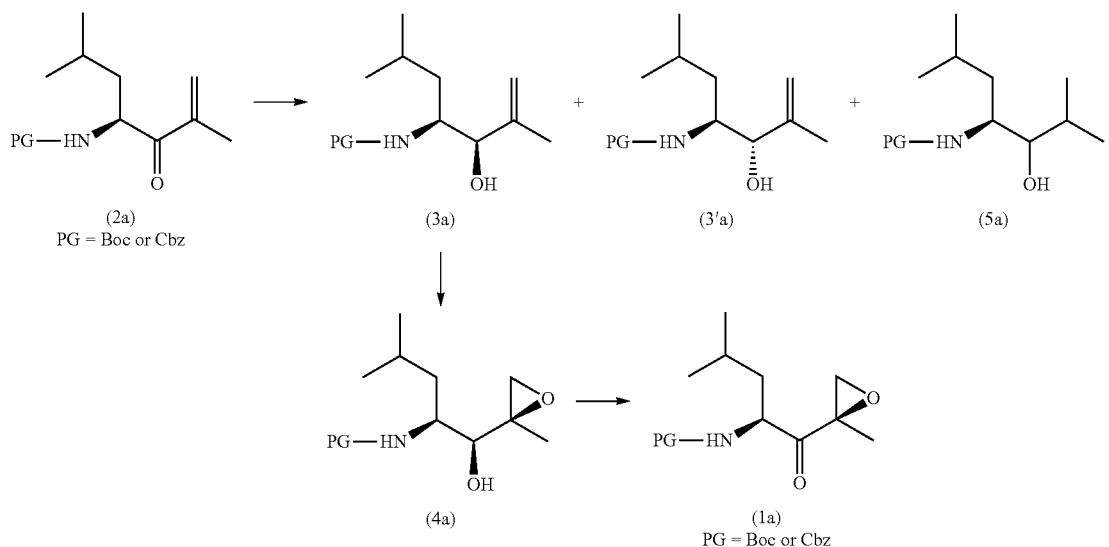

(Patent Document 3)

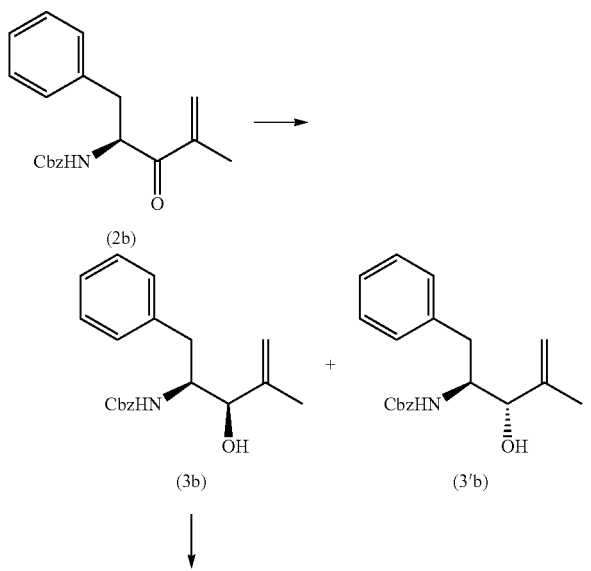

On the other hand, according to the method disclosed in Patent Document 3, when an α,β-unsaturated ketone (2b) is reduced by means of CeCl₃/NaBH₄, the production ratio of (3b) to (3'b) is 5:1. Thus, in any method, it is difficult to produce the desired epoxyketone compound at high selectivity and in good yield.

Further, in Patent Documents 1, 2 and 3, a Swern oxidation reaction or Dess-Martin periodinane is used in order to obtain (1a) or (1b) from an epoxy alcohol compound (4a) or (4b), and, as such, the method can hardly be regarded as an industrially suitable method from the viewpoint of environment and safety.

The present invention has been made in view of such situations, and it is an object of the present invention to provide a method for producing an industrially useful epoxyketone compound, whereby an epoxyketone compound (1a) or (1b) can be obtained in good yield and at high selectivity.

Solution to Problem

In order to accomplish the above object, the present inventors have conducted an extensive study on a method for producing an epoxyketone compound which makes mass production possible with high efficiency, and as a result, have found a method whereby the desired product can be obtained at high stereoselectivity and in good yield and under industrially suitable conditions, and have accomplished the present invention.

That is, the present invention provides the following:

1. A method for producing an alcohol compound represented by the formula (3):

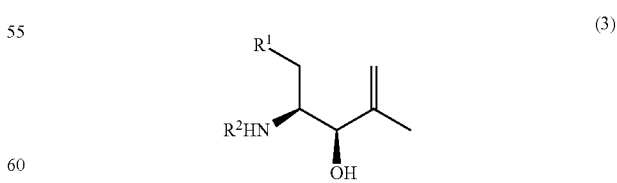

wherein $R^1$ is a hydrogen atom, a linear, branched or cyclic alkyl group, an aromatic group which may have a substituent, or a heterocyclic group which may have a substituent, and $R^2$ is a protective group for an amino group, which comprises reducing a compound represented by the formula (2):

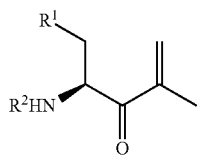

(2)

wherein R¹ and R² are as defined above, in the presence of an amine borane complex represented by R₃N.BH₃, wherein R is a hydrogen atom or a $C_{1-10}$ alkyl group, and R's may be the same or different, provided that at least one R is a $C_{1-10}$ alkyl group.

2. The method according to the above 1, wherein R¹ is an isopropyl group.

3. The method according to the above 1, wherein R¹ is a phenyl group.

4. The method according to any one of the above 1 to 3, wherein R² is a t-butyloxycarbonyl group or a benzyloxycarbonyl group.

5. A method for producing an epoxyketone compound represented by the formula (1):

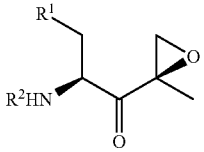

(1)

wherein R¹ is a hydrogen atom, a linear, branched or cyclic alkyl group, an aromatic group which may have a substituent, or a heterocyclic group which may have a substituent, and R² is a protective group for an amino group, which comprises oxidizing an alcohol compound represented by the formula (4):

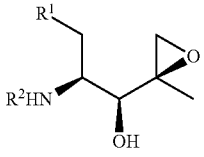

(4)

wherein R¹ and R² are as defined above, by means of an oxidizing agent in the presence of an N-hydroxy compound represented by the formula (6):

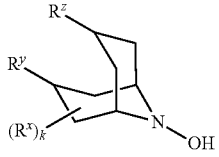

(6)

wherein $R^x$ is at least one substituent selected from a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a $(C_{1-12}$ alkyl)oxy group, a $(C_{3-12}$ cycloalkyl)oxy group, a $(C_{1-12}$ alkyl)thio group, a $(C_{3-12}$ cycloalkyl)thio group, a $(C_{1-12}$ alkyl)amino group, a $(C_{3-12}$ cycloalkyl)amino group, a di($C_{1-6}$ alkyl)amino group, a di($C_{3-6}$ cycloalkyl)amino group, a $C_{1-12}$ alkylcarbonyl group, a $C_{3-12}$ cycloalkylcarbonyl group, a $(C_{1-12}$ alkyl)oxycarbonyl group, a $(C_{3-12}$ cycloalkyl)oxycarbonyl group, a $(C_{1-12}$ alkyl)thiocarbonyl group, a $(C_{3-12}$ cycloalkyl)thiocarbonyl group, a $(C_{1-12}$ alkyl)aminocarbonyl group, a $(C_{3-12}$ cycloalkyl)aminocarbonyl group, a di($C_{1-6}$ alkyl)aminocarbonyl group, a di($C_{3-6}$ cycloalkyl)aminocarbonyl group, a $(C_{1-12}$ alkyl)carbonyloxy group, a $(C_{3-12}$ cycloalkyl) carbonyloxy group, a $(C_{1-12}$ alkyl)carbonylthio group, a $(C_{3-12}$ cycloalkyl) carbonylthio group, a $(C_{1-12}$ alkyl)carbonylamino group, a $(C_{3-12}$ cycloalkyl) carbonylamino group, a di($C_{1-12}$ alkylcarbonyl) amino group, a di($C_{3-12}$ cycloalkylcarbonyl)amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group which may be substituted by $R^a$, a benzyloxy group which may be substituted by $R^a$, a benzylthio group which may be substituted by $R^a$, a benzylamino group which may be substituted by $R^a$, a dibenzylamino group which may be substituted by $R^a$, a benzylcarbonyl group which may be substituted by $R^a$, a benzyloxycarbonyl group which may be substituted by $R^a$, a benzylthiocarbonyl group which may be substituted by $R^a$, a benzylaminocarbonyl group which may be substituted by $R^a$, a dibenzylaminocarbonyl group which may be substituted by $R^a$, a benzylcarbonyloxy group which may be substituted by $R^a$, a benzylcarbonylthio group which may be substituted by $R^a$, a benzylcarbonylamino group which may be substituted by $R^a$, a di(benzylcarbonyl)amino group which may be substituted by $R^a$, an aryl group which may be substituted by $R^a$, an aryloxy group which may be substituted by $R^a$, an arylthio group which may be substituted by $R^a$, an arylamino group which may be substituted by $R^a$, a diarylamino group which may be substituted by $R^a$, an arylcarbonyl group which may be substituted by $R^a$, an aryloxycarbonyl group which may be substituted by $R^a$, an arylthiocarbonyl group which may be substituted by $R^a$, an arylaminocarbonyl group which may be substituted by $R^a$, a diarylaminocarbonyl group which may be substituted by $R^a$, an arylcarbonyloxy group which may be substituted by $R^a$, an arylcarbonylthio group which may be substituted by $R^a$, an arylcarbonylamino group which may be substituted by $R^a$, and a di(arylcarbonyl)amino group which may be substituted by $R^a$, k is an integer of from 0 to 12 and when k is two or more, the respective $R^x$ may be the same or different, each of $R^y$ and $R^z$ which are independent of each other, is a hydrogen atom or $R^x$, or $R^y$ and $R^z$ together form methylene which may be substituted by one or the same or different two $R^x$, and $R^a$ is halogen, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_2$-$C_6$ haloalkynylsulfonyl group, $NO_2$, CN, a formyl group, OH, SH, $NH_2$, SCN, a $C_{1-6}$ alkoxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di-$C_{1-6}$ alkylamino group, the number of $R^a$ to be substituted, is from 1 to 5, and when $R^a$ is two or more, the respective substituents may be the same or different.

6. The method according to the above 5, wherein $R^1$ is an isopropyl group.

7. The method according to the above 5, wherein $R^1$ is a phenyl group.

8. The method according to any one of the above 5 to 7, wherein $R^2$ is a t-butyloxycarbonyl group or a benzyloxycarbonyl group.

9. An epoxy alcohol compound represented by the formula (7):

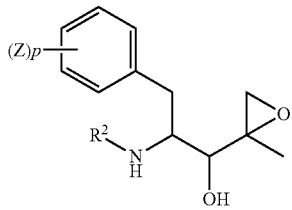

(7)

wherein $R^2$ is —C(O)OR$^b$, R$^b$ is a $C_{1-6}$ alkyl group, Z is a halogen atom, a nitro group, a cyano group, a $C_{1-6}$ alkyl group or a $C_{1-6}$ haloalkyl group, and p is an integer of 0, 1, 2, 3, 4 or 5.

Advantageous Effects of the Invention

According to the present invention, it is possible to produce an epoxyketone compound represented by the formula (1) useful as an intermediate of medicine, highly selectively under mild conditions in good yield and in a large amount. Thus, the production method of the present invention is highly valuable as an industrial method.

DESCRIPTION OF EMBODIMENTS

Now, the present invention will be described in detail.

In the following, n represents normal, i represents iso, s represents secondary, t represents tertiary, c represents cyclo, o represents ortho, m represents meta, and p represents para.

In the present invention, an alkyl group is not particularly limited so long as it is a linear, branched or cyclic alkyl group, but it is preferably a $C_{1-10}$ alkyl group and may, for example, be methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl or n-decyl.

R is preferably a hydrogen atom or the above alkyl group.

Hereinafter, a compound represented by the formula (X) will be referred to simply as a compound (X).

The method for producing the compound (1) of the present invention is shown by the following scheme.

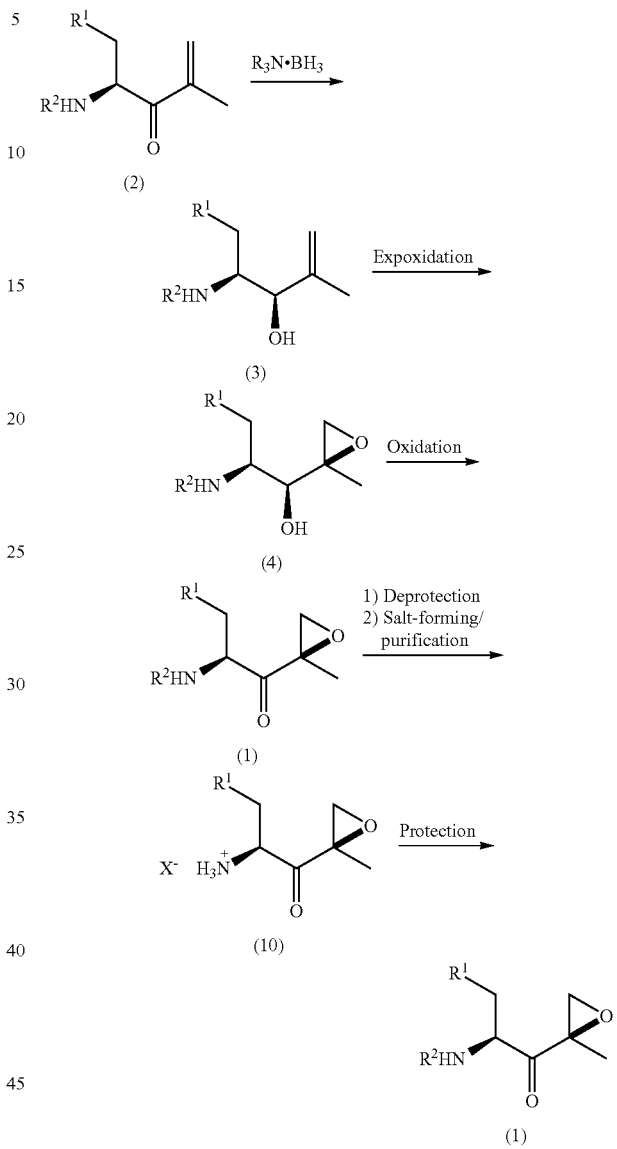

In the above formulae, $R^1$ is a hydrogen atom, a linear, branched or cyclic alkyl group, an aromatic group which may have a substituent, or a heterocyclic group which may have a substituent, and $R^2$ is a protective group for an amino group. The substituent in the "group which may have a substituent" may, for example, be an alkyl group, an alkoxy group, a haloalkyl group, a haloalkoxy group or a cyano group.

$R^1$ may, for example, be a hydrogen atom, a phenyl group or an isopropyl group.

$R^2$ may, for example, be an acyl group, a carbamate group or a sulfonyl group, which is commonly used as a protective group for an amino group.

Specifically, it may, for example, be a protective group to form a carbamate such as a t-butoxycarbonyl group, a benzyloxycarbonyl group, a 9-fluorenylmethyloxycarbonyl group, a 2,2,2-trichloroethoxycarbonyl group or an allyloxycarbonyl group, a protective group to form an amide such as a trifluoroacetyl group, a protective group to form an imide such as a phthaloyl group, or a protective group to form a sulfonamide such as a p-toluenesulfonyl group or a 2-nitrobenzenesulfonyl group. Preferred are a t-butoxycarbonyl group and a benzyloxycarbonyl group.

Now, the production method of the present invention, i.e. the method for producing a compound (3) which comprises reducing a compound (2) in the presence of an amine borane complex, will be described.

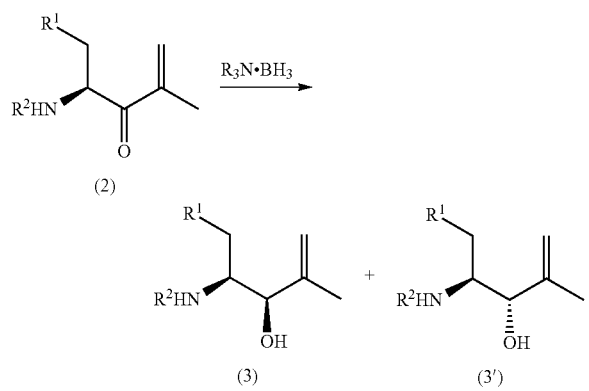

The amine borane complex represented by $R_3N \cdot BH_3$ may be a commercially available product or one prepared by a known method. A preparation method as disclosed by R. F. Borch, S. R. Levitan in J. Org. Chem., 1972, 2347 may, for example, be referred to. Further, such an amine borane complex may be formed in the system and used, as it is, for the reaction.

As $R_3N$, a primary, secondary or tertiary amine may be used, and it may be an optically active substance or a racemic substance.

The primary amine may, for example, be methylamine, ethylamine, n-propylamine, i-propylamine, n-butylamine, i-butylamine, t-butylamine, n-pentylamine, n-hexylamine, c-hexylamine, 2-methyl-c-hexylamine, aniline, benzylamine (phenylmethylamine), 1-phenylethylamine, 2-phenylmethylamine, 1-phenylpropylamine, 1-phenylbutylamine, diphenylethylenediamine, diphenylmethylamine or triphenylmethylamine.

The secondary amine may, for example, be dimethylamine, diethylamine, di-n-propylamine, di-i-propylamine, di-n-butylamine, di-i-butylamine, di-n-pentylamine, di-n-hexylamine, di-c-hexylamine, diphenylamine, diphenylmethylamine, di-1-phenylethylamine, di-2-phenylmethylamine, morpholine, piperidine or pyrrole.

The tertiary amine may, for example, be trimethylamine, triethylamine, tri-n-propylamine, tri-i-propylamine, tri-n-butylamine, tri-i-butylamine, tri-n-pentylamine, tri-n-hexylamine, tri-c-hexylamine, triphenylamine, di-i-propylethylamine, pyridine, quinoline or triazine.

Particularly from the viewpoint of the stereoselectivity and reaction yield, it is preferred to employ an amine borane complex obtained by using an amine having a relatively bulky substituent. Specifically, it is more preferred to employ e.g. a t-butylamine-borane complex, a di-i-propylamine-borane complex or a di-c-hexylamine-borane complex.

The amount of the amine borane complex to be used, is preferably from 0.5 to 1.4 molar equivalent, more preferably from 0.5 to 1.2 molar equivalent, further preferably from 0.7 to 1.2 molar equivalent, to 1 molar equivalent of the compound (4).

The solvent for the reaction is not particularly limited so long as it is stable under the reaction conditions and inert to the reaction.

Solvents which may be used, include, for example, alcohols (methanol, ethanol, propanol, butanol, octanol, etc.), cellosolves (methoxyethanol, ethoxyethanol, etc.), aprotic polar organic solvents (dimethylformamide, dimethylsulfoxide, dimethylacetamide, tetramethylurea, sulfolane, N-methylpyrrolidone, N,N-dimethylimidazolidinone, etc.), ethers (diethyl ether, diisopropyl ether, t-butyl methyl ether, tetrahydrofuran, dioxane, etc.), aliphatic hydrocarbons (pentane, hexane, c-hexane, heptane, octane, decane, decalin, petroleum ether, etc.), aromatic hydrocarbons (benzene, chlorobenzene, o-dichlorobenzene, nitrobenzene, toluene, xylene, mesitylene, tetralin, etc.), halogenated hydrocarbons (chloroform, dichloromethane, dichloroethane, carbon tetrachloride, etc.), alkoxyalkanes (dimethoxyethane, diethoxyethane, etc.), nitriles (acetonitrile, propionitrile, butyronitrile, etc.), etc., but are not limited thereto. These solvents may suitably be selected for use depending upon efficiency of the reaction therein, and may be used alone, respectively, or in combination as a mixture of two or more of them. In the present invention, toluene is particularly preferred among them.

The reaction may be carried out within a temperature range of from −30 to 30° C., but the reaction temperature is more preferably in the vicinity of from −20 to −15° C.

The compound (2) to be used in the present invention can be produced by known methods or methods disclosed in Non-patent Document 1 and Patent Document 3, by using, as a starting material, an amino acid such as L-leucine or L-phenylalanine.

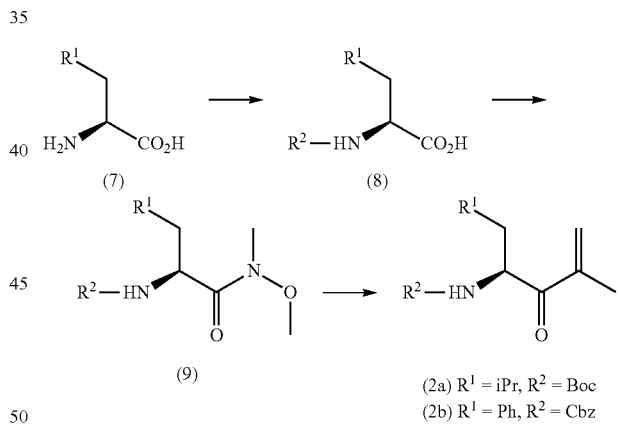

That is, an amino acid represented by the formula (7) is protected by a protective group such as a t-butyloxycarbonyl group (Boc group) or a benzyloxycarbonyl group (Cbz group) by a known method, then reacted with an N,O-dimethylhydroxylamine by a method disclosed in Patent Document 2 to obtain a compound (9). Then, by a method disclosed in Patent Document 2, the compound (9) is reacted with isopropenyl magnesium bromide to obtain e.g. a compound (2a) wherein $R^1$ is an isopropyl group, and $R^2$ is a t-butyloxycarbonyl group, or a compound (2b) wherein $R^1$ is a phenyl group, and $R^2$ is a benzyloxycarbonyl group.

As the compound (2) to be used in the present invention, a purified one may be used, or one obtained from the compound (9) may be used without being isolated. Further, it is also possible to use, without purification, a compound (2)

obtained by using, as a starting material without purification, a compound (9) synthesized by the method disclosed in Patent Document 2.

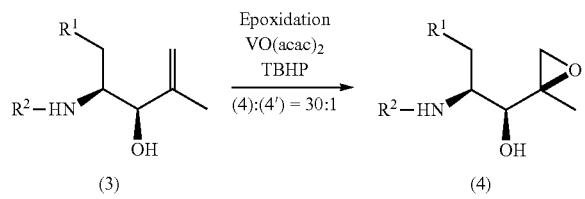

(3)

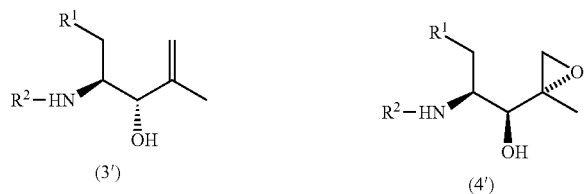

(3')

The compound (3) obtained by the present invention can be led to a compound (4) by epoxidation by a method disclosed in Patent Document 1.

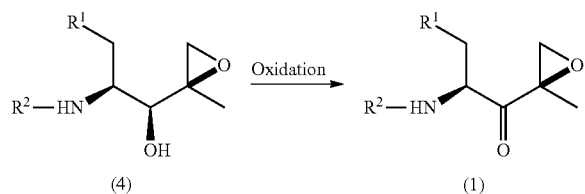

(4) (1)

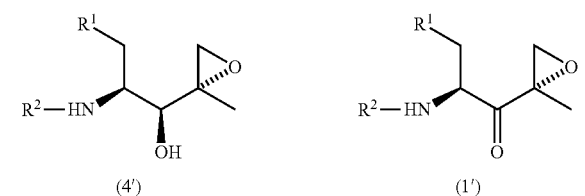

(4') (1')

By oxidizing the compound (4), the compound (1) is obtainable. The compound (1) can be obtained by oxidizing the compound (4) by means of an oxidizing agent in the presence of an N-hydroxy compound represented by the formula (6).

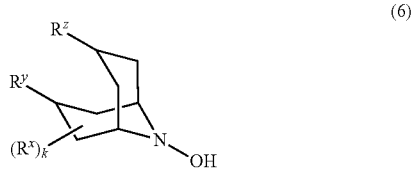

(6)

The N-hydroxy compound represented by the formula (6) may, for example, be N-hydroxy-2-azaadamantane, N-hydroxy-1-methyl-2-azaadamantane, or an N-hydroxy-2-azaadamantane compound having a hydroxy group or a fluorine atom independently substituted at the 5-position and/or 7-position. Among them, preferred is, for example, N-hydroxy-2-azaadamantane, 1-fluoro-N-hydroxy-2-azaadamantane, 5-fluoro-N-hydroxy-2-azaadamantane, 5-fluoro-N-hydroxy-1-methyl-2-azaadamantane, 5,7-difluoro-N-hydroxy-1-methyl-2-azaadamantane, N-hydroxy-1-methyl-2-azaadamantane, N-hydroxy-5-hydroxy-1-methyl-2-azaadamantane, N-hydroxy-5-methoxy-1-methyl-2-azaadamantane, N-hydroxy-5-hydroxy-2-azaadamantane or N-hydroxy-9-azabicyclo[3.3.1]nonane, and particularly preferred is N-hydroxy-2-azaadamantane.

Some of such N-hydroxy compounds are available as commercial products, and some of them can be produced with reference to the disclosures in WO2009/145323, WO2006/001387, US Patent Application Publication No. 2008-0221331A1 and J. Am. Chem. Soc., Vol. 95, No. 19, p 6395-6400 (1973).

The amount of the N-hydroxy compound to be used is preferably from 0.1 mol % to 50 mol %, more preferably from 1 mol % to 10 mol %, to the compound (4) as the substrate.

The oxidizing agent may, for example, be an oxygen-containing organic or inorganic compound. Typically, peracids such as peracetic acid, hydrogen peroxide ($H_2O_2$), hypohalites, halites, halides, diacetoxyiodoarenes, oxygen, or combinations thereof may be mentioned. As hypohalites, alkalimetal hypohalites or alkaline earth metal hypohalites are preferred, and LiOCl, NaOCl, KOCl, LiOBr, NaOBr, KOBr, etc. may be mentioned. Specifically, as the oxidizing agent, an alkali metal hypohalite is preferred, and in the present invention, sodium hypochlorite is particularly preferred.

The amount of the N-hydroxy compound to be used is from 1 mol % to 100 mol %, preferably from 1 mol % to 50 mol %, based on the alcohol as the substrate.

With respect to the temperature for the reaction, the reaction may be carried out at room temperature, but as the case requires, it may be carried out within a range of from 10° C. to 40° C., further within a range of from 0° C. to 100° C., still further within a range of from −10° C. to 200° C. Further, with respect to the pressure for the reaction, normal pressure (the atmospheric pressure) is sufficient, but, as the case requires, the reaction may be carried out in a reduced pressure or increasing pressure state within a range of from 0.01 to 10 MPa.

The reaction time is from 1 minute to 100 hours, preferably from 5 minutes to 24 hours.

The solvent for the oxidation reaction is not particularly limited so long as it is one not to hinder the progress of the reaction. It includes, for example, solvents such as water, aprotic polar organic solvents (e.g. dimethylformamide, dimethylsulfoxide, dimethylacetamide, tetramethylurea, sulforane, N-methylpyrrolidone, N,N-dimethylimidazolidinone, etc.), ethers (e.g. diethyl ether, diisopropyl ether, t-butyl methyl ether, tetrahydrofuran, dioxane, etc.), aliphatic hydrocarbons (e.g. pentane, hexane, c-hexane, octane, decane, decalin, petroleum ether, etc.), aromatic hydrocarbons (benzene, chlorobenzene, o-dichlorobenzene, nitrobenzene, toluene, xylene, mesitylene, tetralin, etc.), halogenated hydrocarbons (e.g. chloroform, dichloromethane, dichloroethane, carbon tetrachloride, etc.), ketones (acetone, methyl ethyl ketone, methyl butyl ketone, methyl isobutyl ketone, etc.), lower fatty acid esters (e.g. methyl acetate, ethyl acetate, butyl acetate, methyl propionate, etc.), alkoxy alkanes (e.g. dimethoxyethane, diethoxyethane, etc.), nitriles (e.g. acetonitrile, propionitrile, butyronitrile, etc.), carboxylic acids (acetic acid, etc.), etc. Among them, toluene, dichloromethane and acetic acid, are, for example, preferred.

Further, as a solvent or as an additive, it is preferred to use acetic acid.

The concentration of (4) as the substrate in the solvent is preferably from 1 to 99 mass %.

In the present invention, as oxygen to be an oxidizing agent, it is possible to use not only oxygen gas (100% oxygen) but also the air.

In the present invention, after confirming disappearance of the compound (4) as the substrate and formation of the compound (1), the compound (1) can be isolated by a usual purification operation such as distillation of the solvent, extraction, recrystallization, filtration, decantation or column chromatography.

The compound (1) may be deprotected by the method disclosed in Patent Document 2 to form an ammonium salt, followed by purification.

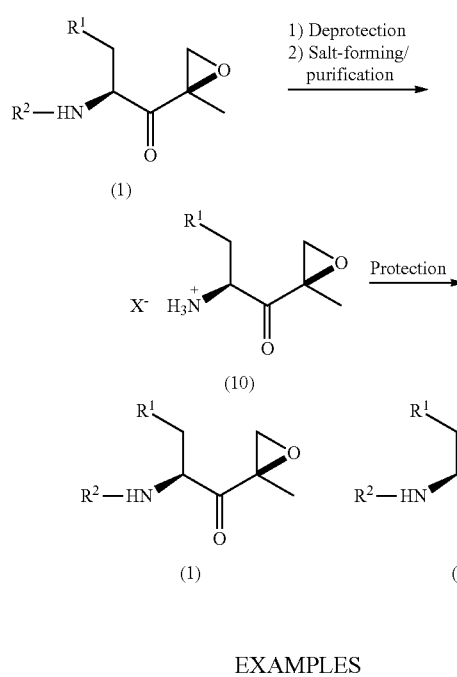

EXAMPLES

Now, the present invention will be described in further detail with reference to Examples and Comparative Examples, but it should be understood that the present invention is by no means restricted by the following Examples.

Here, in the following Examples 1 to 6 and Comparative Examples 1 to 4, the magnetic resonance spectrum ($^1$H-NMR) measurement, the liquid chromatography analysis (LC), and the liquid chromatography mass spectrometry (LC-MS) were carried out by means of the following instruments and the following conditions.

[1] $^1$H-NMR
Apparatus: JNM-ECP300 (manufactured by JEOL, 300 MHz)
Solvent for the measurement: CDCl$_3$, DMSO-d$_6$
[2] LC
(1) LC Condition Example 1: Method Name LC-1
LC: Shimadzu 20A
Column: Xbridge C18 4.6×150 mm 3.5 J.lm (Waters)
Oven Temp: 40° C.
Eluent: CH3CN, 5 mM phosphate buffer
CH$_3$CN=25% (0 min.)→800/0 (25 min.)→80% (30 min.)→25% (30.01 min.)→25% (40 min.) The time program in brackets ( ) represents the total time from the initiation of the analysis.
Flow rate: 1.2 mL/min.
Detector: UV195 nm (2) LC Condition Example 2: Method Name LC-2
LC: Shimadzu 20A
Column: CAPCELLPAK C18 MG1I4.6×100 mm 3 μM (Shiseido)
Oven Temp: 40° C.
Eluent: CH$_3$CN, 5 mM phosphate buffer
CH$_3$CN=25% (0 min.)→80% (35 min.)→80% (40 min.)→25% (40.01 min.)→25% (45 min.) The time program in brackets ( ) represents the total time from the initiation of the analysis.
Flow rate: 1.2 mL/min.
Detector: UV195 nm
Method for Preparing 5 mM Phosphate Buffer
In 4 L of distilled water, 1.20 g of disodium hydrogen phosphate (anhydrous) and 1.42 g of sodium dihydrogen phosphate (anhydrous) are dissolved, and is confirmed by a pH meter that the pH is within a range of from 6.5 to 7.0.
[3] LC-MS
LC-MS: Waters 2695, MICROMASS QUATTRO MICROAPI
Eluent: CH$_3$CN, 5 mM ammonium acetate aqueous solution
With respect to the analytical conditions, the analysis was carried out by the same method as in LC except for Eluent.

Example 1

Preparation of Compound (3)

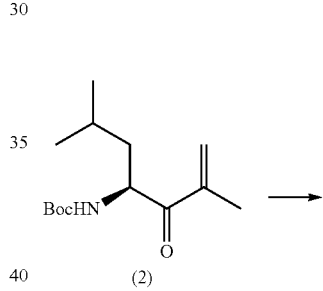

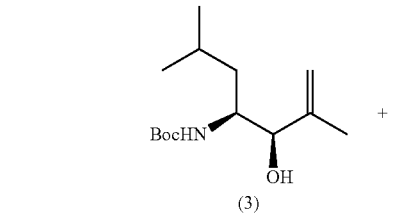

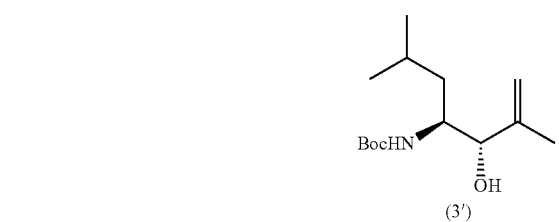

A solution of the compound (2) (9.0 g) in toluene (90.0 g) was cooled to −20° C., and then, a diisopropylamine borane complex solution (32.9 g) was dropwise added, followed by stirring at −15° C. for 4 hours, whereupon disappearance of the starting material was confirmed by LC. To the reaction solution, 3.5% hydrochloric acid (146.9 g) was added at from −15° C. to 0° C., followed by stirring at 25° C. and then by liquid separation. To the water layer, toluene (100 g) was added, followed by liquid separation. The organic layers were mixed, and a 5% sodium hydrogen carbonate aqueous solution (150 g) was added, followed by stirring and then by liquid separation. Further, to the organic layer, water (150 g×2) was added and stirred, and liquid separation was repeated twice.

The organic phase was concentrated, and methanol (18 g) was added, followed by stirring at 25° C., and distilled water (90 g) was dropwise added, whereupon after confirming precipitation of crystals, the system was cooled to 2° C. and stirred for one hour, followed by filtration and drying to obtain the compound (3) as white crystals (8.4 g). The yield of crystals was 92.7%, and the formation ratio of the compound (3) to the stereoisomer (3') was 36.6:1.

LC-MS (ESI+) m/z: 258 (MH+)

LC-1: R.T. 17.03 min/compound (3), 17.56 min/compound (3')

Preparation of Diisopropylamine Borane Complex Solution

A solution of diisopropylamine (5.3 g) in hexane (30.9 g) was cooled to 0° C., and dimethyl sulfide borane (4.0 g) was dropwise added, followed by stirring at 0° C. for one hour, and the solution was used for the reaction.

Identification of Compound (3) and Stereoisomer (3')

Using the compound (2), the reaction was carried out under the same conditions as in paragraph 0465 in Patent Document 2, and an analysis was carried out by LC-1 whereby two peaks at retention times (R.T.) of 17.03 min and 17.56 min by LC-MS (ESI+) m/z: 258 (MH+), were formed at an area ratio of 7.7:1. In paragraph 0465 in Patent Document 2, compounds (3) and (3') are disclosed to form at a LC area ratio of 4.5:1. Accordingly, R.T. 17.03 min was identified to be the compound (3), and R.T. 17.56 min was identified to be the compound (3').

Examples 2-1 to 2-4 and Comparative Examples 1 to 4

Reduction Reaction of Compound (2)

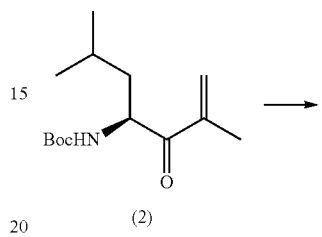

(2)

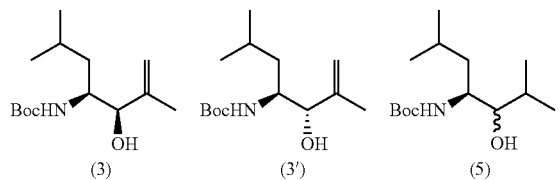

Reduction of the compound (2) was carried out by various reducing agents, whereby the results were summarized in the following Table 1. With respect to each reducing agent, the ratio of (3):(3') is the value obtained by using the most suitable solvent.

TABLE 1

| | Reducing agent | Reaction temperature | Solvent | (3):(3') | Notes |
|---|---|---|---|---|---|
| Ex. 2-1 | Dicyclohexylamine-BH$_3$ | 0° C. | Toluene | 32.5:1 | (3) Yield: 91.3% |
| Ex. 2-2 | Diisopropylamine-BH$_3$ | 0° C. | Toluene | 22.4:1 | (3) Yield: 91.5% |
| Ex. 2-3 | Di-sec-Butylamine-BH$_3$ | 0° C. | Toluene | 21.9:1 | — |
| Ex. 2-4 | Tert-butylamine-BH$_3$ | 0° C. | Toluene | 13.9:1 | — |
| Comp. Ex. 1 | Me$_2$S—BH$_3$ | 0° C. | Toluene | 5.1:1 | Comparative test |
| Comp. Ex. 2 | L-selectride | −78° C. | THF | — | In accordance with Patent Document 1 Only (5) was formed, and (3) and (3') were in trace amounts |
| Comp. Ex. 3 | L-selectride/CeCl$_3$•7H$_2$O | −78° C. | THF | — | Starting material remained, and reaction not proceeded |
| Comp. Ex. 4 | NaBH$_4$/CeCl$_3$•7H$_2$O | 0° C. | MeOH | 7.7:1 | — |

Note:
The molar amount of the reducing agent per 1 mol of the compound (2) as the substrate is the same as in Example 1, in all Examples in the above Table.

Example 3

Preparation of Compound (4)

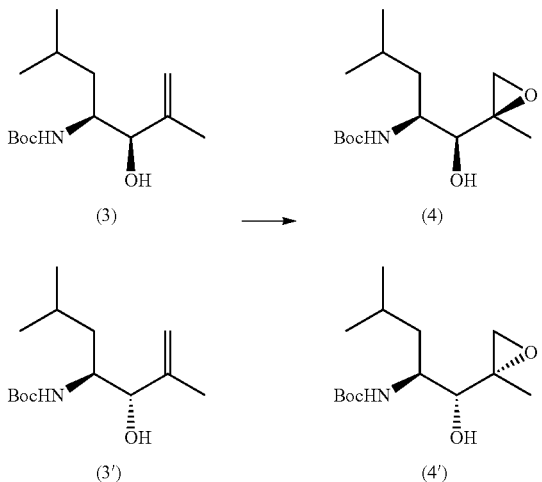 [SMILES: C=C(C)[C@@H](O)[C@H](CC(C)C)NC(=O)OC(C)(C)C ; CC(C)C[C@H](NC(=O)OC(C)(C)C)[C@H](O)[C@@]1(C)CO1 ; C=C(C)[C@H](O)[C@H](CC(C)C)NC(=O)OC(C)(C)C ; CC(C)C[C@H](NC(=O)OC(C)(C)C)[C@@H](O)[C@]1(C)CO1]

A solution of compounds (3):(3')=36.6:1 (6.8 g) in dichloromethane (267 mL) was cooled to 0° C., and then vanadium acetylacetonate (70.5 mg) was added and stirred, whereupon a 70% t-butyl hydroperoxide aqueous solution (6.87 g) was dropwise added, followed by stirring at room temperature for one hour. Vanadium acetylacetonate (70.5 mg×4) was added every one hour four times, and by LC (195 nm), it was confirmed that the peak area of the starting material became at most 5% as compared with the product. The reaction solution was filtrated through Celite (6.87 g) and cooled to 0° C., and then, a 10% sodium thiosulfate aqueous solution (126.6 g) and a 10% sodium hydrogen carbonate aqueous solution (67.3 g) were added, followed by stirring for 30 minutes and then by liquid separation. To the aqueous layer, dichloromethane (200 mL) was added, followed by stirring and then by liquid separation. The organic layers were mixed, and distilled water (150 mL) was added and stirred, and liquid separation was carried out twice, followed by concentration to obtain a toluene solution having an about 10% concentration of the compound (4).

LC-MS (ESI+) m/z: 274 (MH+)/compounds (4) and (4')
LC-1: R.T. 13.41 min/compound (4)
Identification of Compound (4)

The compound (4) was isolated by column chromatography, and the reaction in Example 4 was carried out, and the product was analyzed by LC-2, whereby R.T. agreed to compound (1) and thus, it was identified to have a structure of (4).

Example 4

Preparation of Compound (1)

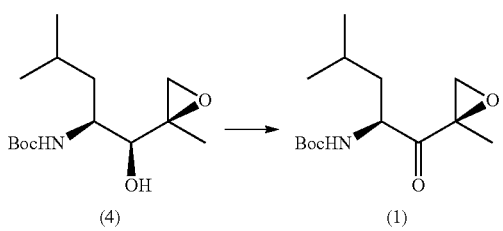 [SMILES: CC(C)C[C@H](NC(=O)OC(C)(C)C)[C@H](O)[C@@]1(C)CO1 ; CC(C)C[C@H](NC(=O)OC(C)(C)C)C(=O)[C@@]1(C)CO1]

The toluene solution (80.14 g) of the compound (4) was cooled to 0° C., and then, N-hydroxy-2-azaadamantane (AZADOL (registered trademark) manufactured by Wako Pure Chemical Industries, Ltd.) (410 mg) was added, followed by stirring, whereupon a 5% sodium hydrogen carbonate aqueous solution (59.6 g) and a 13.7% sodium hypochlorite aqueous solution (23.8 g) were dropwise added, followed by stirring for 3 hours. Then, AZADOL (1.25 g), a 5% sodium hydrogen carbonate aqueous solution (118.6 g) and a 13.7% sodium hypochlorite aqueous solution (47.6 g) were additionally added, followed by stirring for two hours, whereupon disappearance of the starting material was confirmed by LC, and a 10% sodium thiosulfate aqueous solution (87.8 g) and a 5% hydrochloric acid aqueous solution (27.8 g) were added, followed by stirring for 30 minutes and then by liquid separation. To the aqueous layer, toluene (72.9 g) was added, followed by stirring and then by liquid separation. The organic layers were mixed, and a 10% sodium hydrogen carbonate aqueous solution (150 g) was added, followed by stirring and then by liquid separation. To the organic layer, clean water (150 g) was added and stirred, and liquid separation was carried out twice, followed by concentration to obtain the compound (1) (5.96 g). In the entire test from Example 3, the yield from the compound (3) was 83%.

$^1$H-NMR (300 MHz, ppm, in CDCl$_3$) δ: 0.93-0.95 (d, 3H), 0.96-0.98 (d, 3H), 1.15-1.20 (m, 1H), 1.41 (s, 9H), 1.47-1.51 (m, 1H), 1.52 (s, 3H), 1.70-1.77 (m, 1H), 2.88-2.92 (d, 1H), 3.28-3.32 (d, 1H), 4.30-4.34 (dt, 1H), 4.82-4.88 (d, 1H)
LC-MS (ESI+) m/z: 272 (MH+)
LC-2: R.T. 27.14 min

Example 5

Preparation of Compound (10)

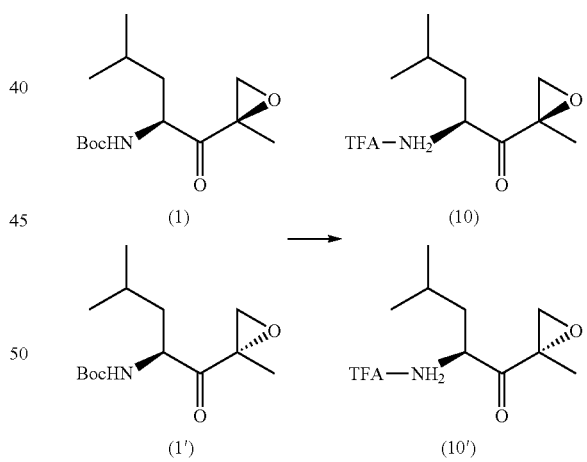

A solution of compounds (1):(1')=28.6:1 (500 mg) in dichloromethane (2 g) was cooled to 0° C., and trifluoroacetic acid (1.05 g) was added, followed by stirring at room temperature for 6 hours. After confirming disappearance of the starting material by LC, concentration was carried out, and methyl-tert-butyl ether (1.5 g) and heptane (3.6 g) were added, followed by stirring at 0° C. for 30 minutes, and then, filtration and washing with heptane (4 g) were carried out to obtain white crystals (432.1 mg) of a mixture of compounds (10) and (10') (the formed ratio was calculated in Example 6).
LC-2: R.T. 7.30 min/compound (10)
LC-MS (ESI+) m/z: 172 (MH+)

Example 6

Preparation of Compound (1)

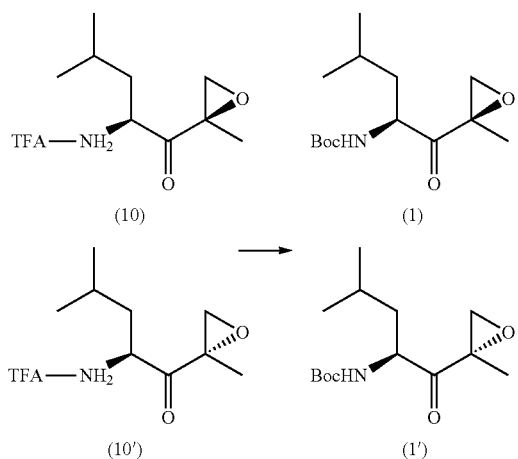

A solution of compounds (10) and (10') (51 mg) in dichloromethane (500 mg) was cooled to 0° C., and then, triethylamine (47.1 mg) and di-tert-butyl dicarbonate (64.6 mg) were added, followed by stirring at room temperature for 13 hours. After confirming disappearance of the starting material by LC, the system was cooled to 0° C., and then, a 7% hydrochloric acid aqueous solution (460 mg) was added and stirred, and then liquid separation was repeated twice. Thereafter, a 5% sodium hydrogen carbonate aqueous solution (500 mg) was added and stirred, and liquid separation was repeated twice. Clean water (500 mg) was added and stirred, and liquid separation was repeated twice to obtain an organic layer (29 mg). In the entire test from Example 5, the formed ratio of the obtained compound (1) to the stereoisomer (1') was 53.5:1, and the yield was 39%.

$^1$H-NMR (300 MHz, ppm, in CDCl$_3$) δ: 0.93-0.95 (d, 3H), 0.96-0.98 (d, 3H), 1.15-1.20 (m, 1H), 1.41 (s, 9H), 1.47-1.51 (m, 1H), 1.52 (s, 3H), 1.70-1.77 (m, 1H), 2.88-2.92 (d, 1H), 3.28-3.32 (d, 1H), 4.30-4.34 (dt, 1H), 4.82-4.88 (d, 1H)/compound (1)

LC-MS (ESI+) m/z: 272 (MH+)/compounds (1) and (1')

LC-2: R.T. 27.14 min/compound (1), 25.00 min/compound (1')

Identification of Compound (1)

(1') as the stereoisomer was isolated by column chromatography, and the X-ray structural analysis (apparatus: SMART APEX II ULTRA X-RAY: CuKα, measuring temperature: −50° C.) was carried out to confirm the structure of compound (1'). On this basis, the structure of the compound (1) as the main product was confirmed to be the above steric structure.

With respect to identification of compound 1, determination was also made in accordance with the following method.

That is, the compound (1) [5.12 g, the ratio of compound (1) to compound (1') being 3.3:1] obtained in accordance with the method disclosed in Example 4 was purified by column chromatography to obtain compound (1) [2.19 g, compound (1') as a stereoisomer was not detected] as a colorless transparent viscous liquid. After the purification, the compound was kept refrigerated at −20° C. for 24 hours, and white crystals of the compound (I) obtained by imparting a stimulus by a spatula were subjected to an X-ray structural analysis, whereby it was confirmed that the compound (1) had a "S" configuration at the 2-position and a "R" configuration at the 4-position.

Here, the column chromatography and the X-ray structural analysis in the identification of compound (1) were carried out under the following conditions.

Column Chromatography;

Column used: Hi-Flash Column, 40 μm, 60 Å, 130 g

Gradient composition: hexane/ethyl acetate=100/0 (5 min.) →97/3 (25 min.)→97/3 (45 min.)→95/5 (65 min.)→95/5 (95 min.)

(The time program in brackets represents the total time from the initiation of column.)

X-Ray Structural Analysis;

Apparatus name: SMART APEXII ULTRA

X-ray: Cu-Kα

Temperature for measurement: −100° C.

Purification of Compound (1) by Crystallization

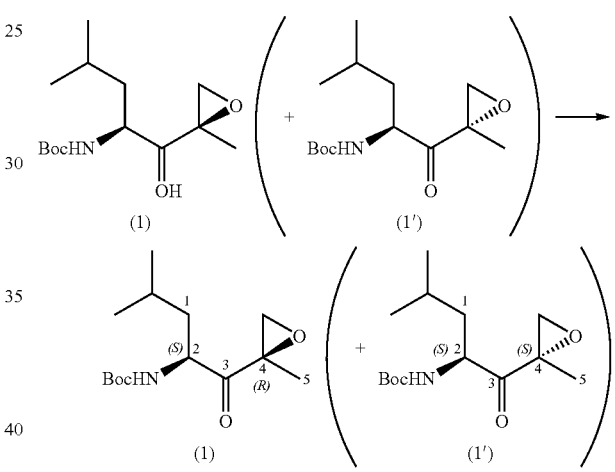

To the compound (1) [1.84 g, the ratio of the compound (1) to the compound (1') as its steric isomer being 45.1:1] obtained in accordance with the method disclosed in Example 4, ethanol (4.81 g), N,N-dimethylformamide (4.80 g) and water (4.81 g) were added. After completion of the addition, the solution was heated to about 55° C., and after confirming that the compound (1) was all dissolved in the added solvents, the solution was cooled to 2.2° C. After completion of the cooling, at the same temperature, the white crystals of the compound (1) obtained in the identification of compound (1) in Example 6 were added as seed crystals (1.84 mg). After completion of the addition, the solution was stirred for 1 hour. After completion of the stirring, water (6.72 g) was added to the solution. After completion of the addition, the solution was cooled to −8° C., and stirring was continued for 1 hour. After completion of the stirring, the crystals of the compound (1) precipitated in the solution were separated by an filtration operation. The obtained crystals of the compound (1) were dried under reduced pressure to obtain the compound (1) as slightly yellow crystals (1.73 g). The recovery rate of the compound (1) in this crystallization operation was 94.0%. Further, the ratio of the compound (1) to the compound (1') as its steric isomer was 197.8:1.

Here, identification of the ratio of the compound (1) to the compound (1') was carried out by column chromatography. The analytical conditions were as follows.

LC: Shimadzu 20A

Column: YMC Pack Pro C18 RS 4.6×250 mm 5.0 μm (YMC)

Oven Temp.: 30° C.

Eluent: CH$_3$CN, 5 mM phosphoric acid buffer

CH$_3$CN=10% (5 min.)→80% (25 min.)→80% (32 min.)→10% (32.01 min.)→10% (40 min.) The time program in brackets represents the total time from the initiation of the analysis.

Flow rate: 1.2 mL/min.

Detector: UV195 nm

Liquid Chromatography Analysis (LC)

The liquid chromatography analysis (LC) in the following Examples 7 to 12 was carried out by means of the following instruments and conditions in addition to the above-described analytical conditions (LC-1 and LC-2).

(3) LC Condition Example 3: Method Name LC-3

LC: Shimadzu 20A

Column: YMC Pack Pro C18 RS 4.6×250 mm 5.0 μm (YMC)

Oven Temp: 30° C.

Eluent: CH$_3$CN, 5 mM phosphate buffer

CH$_3$CN=10% (5 min.)→80% (25 min.)→80% (32 min.)→10% (32.01 min.)→10% (40 min.) The time program in brackets ( ) represents the total time from the initiation of the analysis.

Flow rate: 1.2 mL/min.

Detector: UV210 nm (4) LC Condition Example 4: Method Name LC-4

LC: Shimadzu 20A

Column: CAPCELLPAK C18 MGII 4.6×100 mm 3 μm (Shiseido)

Oven Temp: 30° C.

Eluent: CH$_3$CN, 5 mM phosphate buffer

CH$_3$CN=10% (5 min.)→80% (25 min.)→80% (32 min.)→10% (32.01 min.)→10% (40 min.) The time program in brackets ( ) represents the total time from the initiation of the analysis.

Flow rate: 1.2 mL/min.

Detector: UV210 nm

Example 7

Preparation of Compound (3b)

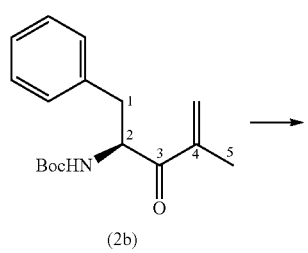

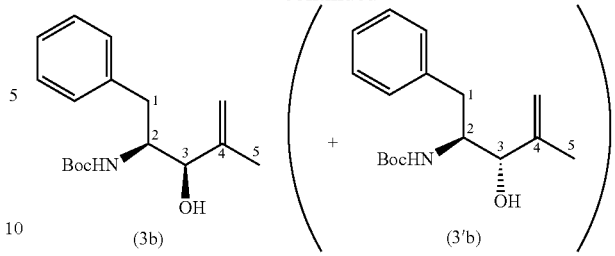

A solution of the compound (2b) (5.8 g) in toluene (29.2 g) was dropwise added to a dicyclohexylamine borane complex solution, while maintaining the temperature between −10° C. and 0° C. After completion of the dropwise addition, the reaction solution was stirred at −5° C. for 5 hours. After completion of the stirring, by an analysis by LC, it was confirmed that the compound (2b) as the starting material was all reacted. After completion of the confirmation, acetone (17.5 g) was added to the reaction solution at −5° C. After completion of the addition, stirring was carried out at 35° C. for 1.5 hours, and then, 2N hydrochloric acid (29.2 g) was added at 25° C. After completion of the addition, stirring was carried out at the same temperature for one hour. After completion of the stirring, the amine hydrochloride precipitated in the reaction solution was separated by a filtration operation, and the obtained filtrate was subjected to liquid separation. To the obtained organic layer, water (25 g×2) was added, and an operation of stirring and liquid separation was repeated twice, whereupon a 3.3% toluene solution of compound (3b) (5.6 g) was obtained. The yield was 95.5%, and the formation ratio of the compound (3b) to the compound (3'b) as a stereoisomer was 18.8:1.

Further, the compound (2b) was prepared in accordance with the method disclosed in Journal of Chinese Pharmaceutical Sciences, 2009, p. 33-36.

Crystallization of Compound (3b)

The 3.3% toluene solution of the compound (3b) (5.6 g) obtained by the above-described method, was concentrated under reduced pressure, and then, dichloromethane (112 g) was added to prepare a dichloromethane solution of the compound (3b). To the dichloromethane solution, activated carbon (special reagent Shirasagi) (1.1 g) was added, followed by stirring at 25° C. for one hour. After completion of the stirring, the activated carbon was separated by a filtration operation, and the obtained filtrate was concentrated under reduced pressure. To the obtained compound (3b), toluene (42 g) was added and then heated to near 60° C. to dissolve all of the compound (3b) in toluene. To the obtained toluene solution, n-heptane (25.2 g) was dropwise added, and after confirming that crystals of the compound (3b) were precipitated, the toluene solution was cooled to −5° C. and stirred for one hour. After completion of the stirring, the compound (3b) precipitated in the toluene solution was separated by a filtration operation. The obtained crystals of the compound (3b) were dried under reduced pressure, whereby the compound (3b) was obtained as white crystals (4.9 g). The yield in this crystallization operation was 88.5%, and the ratio of the compound (3b) to the compound (3'b) as a stereoisomer was 104.2:1.

¹H-NMR (300 MHz, ppm, in CDCl₃) δ: 1.34 (s, 9H), 1.81 (s, 3H), 2.35 (s, 1H), 2.68-2.72 (m, 1H), 2.89 (dd, 1H), 3.99 (s, 1H), 4.20 (s, 1H), 4.65 (s, 1H), 5.00 (s, 1H), 5.08 (s, 1H), 7.18-7.28 (m, 5H)/compound (3b)

LC-MS (ESI+) m/z: 292 (MH+)/compound (3b) and (3'b)

LC-4: R.T. 19.8 min/compound (3b), 20.3 min/compound (3'b)

Preparation of Dicyclohexylamine Borane Complex Solution

A solution of dicyclohexylamine (3.9 g) in toluene (58.4 g) was cooled to −5° C., and then, to this toluene solution, a dimethylsulfide borane complex solution (1.8 g) was dropwise added. After completion of the dropwise addition, stirring was carried out at −5° C. for 0.5 hour to obtain a solution, which was used for the reaction as described in Example 7.

Identification of Steric Configuration of Compound (3b)

The compound (3b) before crystallization, as obtained in accordance with the above-described method, was purified by column chromatography.

The compound (3b) after the purification was subjected to an X-ray structural analysis, whereby it was confirmed that the 2-position of the compound (3b) has a steric configuration of "S" and the 3-position has a steric configuration of "R".

Further, the column chromatography and X-ray structural analysis in the identification of the steric configuration of the compound (3b) were carried out under the following conditions.

Column Chromatography:
Column used: Hi-Flash Column, 40 μm, 60 Å, 14 g
Gradient composition: Hexane/ethyl acetate=100/0 (4 min.)→90/10 (12 min.)→90/10 (32 min.)→85/15 (44 min.)→85/15 (68 min.)→80/20 (80 min.)→80/20 (104 min.)→75/25 (116 min.) The time program in brackets ( ) represents the total time from the initiation of the analysis.

X-Ray Structural Analysis:
Apparatus: SMART APEX II ULTRA
X-ray: Cu-Kα
Measuring temperature: −50° C.

Examples 8-1 to 8-13

Study of Reducing Agent in Reduction Reaction of Compound (2b)

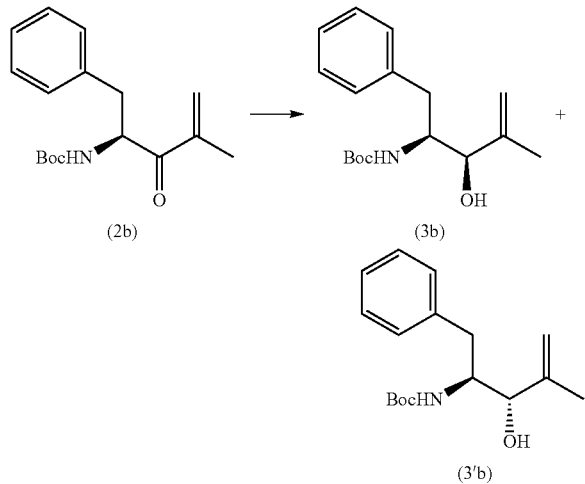

In the reduction reaction of the compound (2b), the results relating to the yield and the isomer ratio at the time of studying the reducing agent are summarized in the following Table 2. The reaction conditions, analytical conditions, etc. were in accordance with those disclosed in Example 7. In all Examples in the following Table, the reaction temperature was −5° C., the solvent was toluene, and the reducing agent was used in an amount of 1.05 equivalent to the compound (2b).

TABLE 2

| Ex. No. | Reducing agent | Ratio Compound (3b):(3'b) | Yield of compound (3b) (%) |
|---------|----------------|---------------------------|----------------------------|
| 8-1 | Dicyclohexylamine-BH₃ | 18.8:1 | 90.6 |
| 8-2 | Cyclohexyl-isopropylamine-BH₃ | 13.7:1 | 85.5 |
| 8-3 | t-Butylamine-BH₃ | 10.4:1 | 86.5 |
| 8-4 | N-Cyclohexyl-aniline-BH₃ | 10.2:1 | 86.4 |
| 8-5 | Diisopropylamine-BH₃ | 9.8:1 | 85.4 |
| 8-6 | Cyclohexyl-methylamine-BH₃ | 8.7:1 | 84.4 |
| 8-7 | Diisoamylamine-BH₃ | 8.3:1 | 83.1 |
| 8-8 | t-Butyl-methylamine-BH₃ | 7.8:1 | 85.6 |
| 8-9 | (S)-Phenylethylamine-BH₃ | 7.6:1 | 86.8 |
| 8-10 | (R)-Phenylethylamine-BH₃ | 6.2:1 | 82.1 |
| 8-11 | Morpholine-BH₃ | 6.0:1 | 68.9 |
| 8-12 | Cyclohexylamine-BH₃ | 5.4:1 | 80.4 |
| 8-13 | Cyclopentylamine-BH₃ | 4.9:1 | 81.4 |

Example 9

Preparation of Compound (4b)

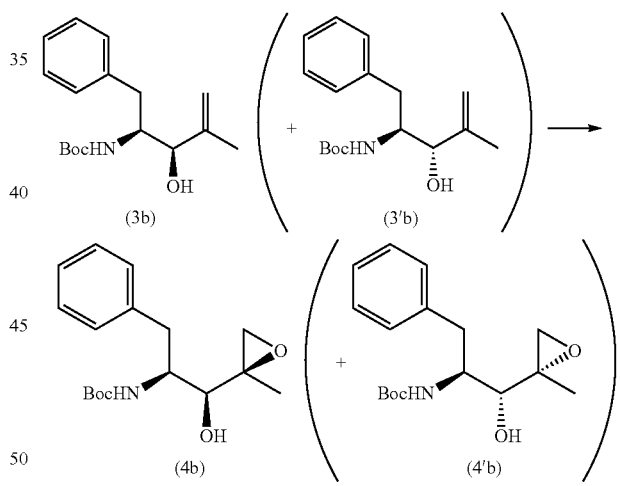

A solution of 3.0 g of the compound (3b) [a mixture with the compound (3'b), and the ratio is (3b):(3'b)=104.2:1] in dichloromethane (24.0 g) and water (6.0 g), was cooled to 0° C., and then, vanadium acetyl acetonate (34.1 mg) was added. After completion of the addition, to the reaction solution, a 70 wt % t-butyl hydroperoxide aqueous solution (2.7 g) was dropwise added. After completion of the dropwise addition, the reaction solution was stirred at 25° C. for 4 hours. After completion of the stirring, by the analysis by LC, it was confirmed that the peak area of the compounds (3b) and (3'b) as the starting material became at most 5% as compared with the peak area of the compounds (4b) and (4'b) as the product. After completion of the confirmation, to the reaction solution, a 10 wt % sodium thiosulfate aqueous solution (32.0 g) and then a 5 wt % sodium hydrogen carbonate aqueous solution (43.0 g) were added. After completion of the addition, the reaction solution was stirred for 30 minutes, followed by a liquid separation operation. To the obtained organic layer, water (37.5 g×2) was added, and then the stirring and liquid separation operation was repeated twice. The obtained organic layer was concentrated under reduced pressure to obtain the compound (4b) as yellow crystals (3.03 g). The yield was 95.2%. The obtained compound (4b) was subjected to a LC-MS analysis under the following analytical conditions, whereby a peak showing the same MS as the compound (4b) was observed in a very small amount. This is assumed to be the compound (4'b) as an isomer of the compound (4b), derived from the compound (3'b).

$^1$H-NMR (300 MHz, ppm, in CDCl$_3$) δ: 1.32 (s, 9H), 1.38 (s, 3H), 2.46 (s, 1H), 2.60 (d, 1H), 2.73-2.88 (m, 2H), 3.00 (d, 1H), 3.85 (s, 1H), 4.13 (m, 1H), 4.90 (d, 1H), 7.20-7.29 (m, 5H)/compound (4b)

LC-MS (ESI+) m/z: 308 (MH+)/compound (4b) and (4'b)

LC-3: R.T. 24.1 min/compound (4b), 24.9 min/compound (4'b)

Example 10

Preparation of Compound (1b)

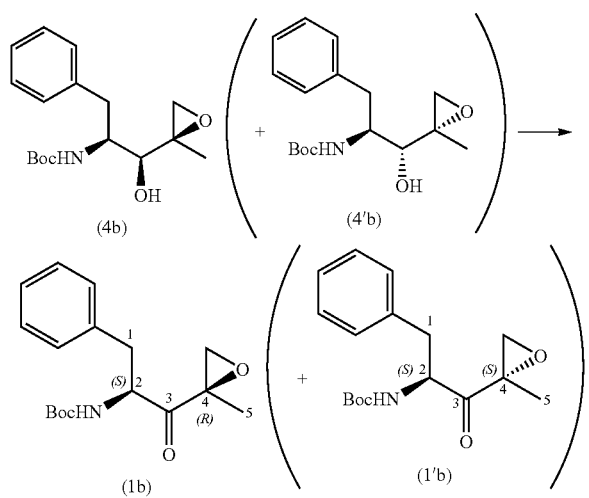

A solution of 3.0 g of the compound (4b) [containing a very small amount of the compound (4'b)] obtained in accordance with the method described in Example 9, in dichloromethane (35.4 g), was cooled to 0° C., and then, N-hydroxy-2-azaadamantane [AZADOL (registered trademark), sold by Wako Pure Chemical Industries, Ltd.] (147 mg) was added. After completion of the addition, to the reaction solution, a 5 wt % sodium hydrogen carbonate aqueous solution (23.9 g) and then a 13.7% sodium hypochlorite aqueous solution (8.5 g) were dropwise added. After the dropwise addition, the reaction solution was stirred at the same temperature for one hour. After completion of the stirring, by the analysis by LC, it was confirmed that all of the compound (4b) as the starting material was reacted. After completion of the confirmation, a 10 wt % sodium thiosulfate aqueous solution (14.9 g) was added and stirred for 30 minutes, followed by liquid separation. To the obtained organic layer, a 0.5 N hydrochloric acid aqueous solution (20.0 g) was added and stirred for 10 minutes, followed by liquid separation. To the obtained organic layer, a 5 wt % sodium hydrogen carbonate aqueous solution (19.9 g) was further added and stirred for 10 minutes, followed by liquid separation. To the obtained organic layer, water (18.8 g×2) was further added and stirred for 10 minutes, followed by liquid separation twice to obtain a 3 wt % dichloromethane solution of the compound (1b) (3.0 g). The yield was 102.6% and the formation ratio of the compound (1b) to the compound (1'b) as a stereoisomer was 26.4:1.

$^1$H-NMR of compound (1b) (300 MHz, ppm, in CDCl$_3$) δ: 1.37 (s, 9H), 1.50 (s, 3H), 2.74 (dd, 1H), 2.90 (d, 1H), 3.10 (dd, 1H), 3.29 (d, 1H), 4.58 (m, 1H), 4.93 (d, 1H), 7.15-7.31 (m, 5H)/

$^1$H-NMR of compound (1'b) (300 MHz, ppm, in CDCl$_3$) δ: 1.40 (s, 9H), 1.49 (s, 3H), 2.58 (d, 1H), 2.67 (d, 1H), 2.83 (m, 1H), 3.01 (m, 1H), 4.67 (m, 1H), 4.89 (m, 1H), 7.13-7.30 (m, 5H)

LC-MS (ESI+) m/z: 306 (MH+)/compound (1b) and (1'b)

LC-3: R.T. 27.9 min/compound (1b), 26.8 min/compound (1'b)

Here, the yield of the compound (1b) after purification was calculated by the quantitative analysis of HPLC. The analytical conditions, etc. of HPLC are shown below.

Standard substance: Compound (1b)

HPLC condition: LC-3

Identification of Steric Configurations of Compounds (1b) and (1'b)

A mixture of the compound (1b) and the compound (1'b) obtained by the above-described method was purified and separated by column chromatography to isolate the compound (1'b). The obtained compound (1'b) was subjected to an X-ray structural analysis, whereby it was confirmed that the 2-position of the compound (1'b) has a steric configuration of "S", and the 4-position has a steric configuration of "S". Further, as the steric configuration of the compound (1'b) was determined, it was ascertained that the 2-position of the compound (1b) as an isomer has a steric configuration of "S", and the 4-position has a steric configuration of "R".

Here, in the identification of the steric configuration of the compound (1'b), the column chromatography and X-ray structural analysis were carried out under the following conditions.

Column Chromatography:

Column used: Hi-Flash Column, 40 µm, 60 Å, 14 g

Gradient composition: Hexane/ethyl acetate=90/10 (5 min.)→80/20 (25 min.)→80/20 (40 min.)→50/50 (50 min.) The time program in brackets ( ) represents the total time from the initiation of the analysis.

X-Ray Structural Analysis:

Apparatus: SMART APEX II ULTRA

X-ray: Cu-Kα

Measuring temperature: −100° C.

Example 11

Purification of Compound (1b)

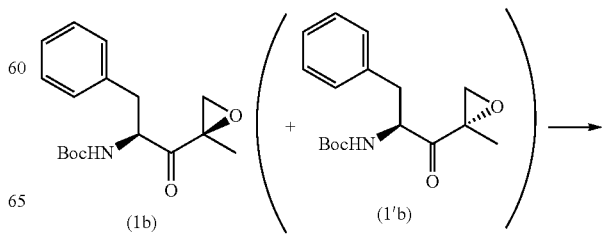

-continued

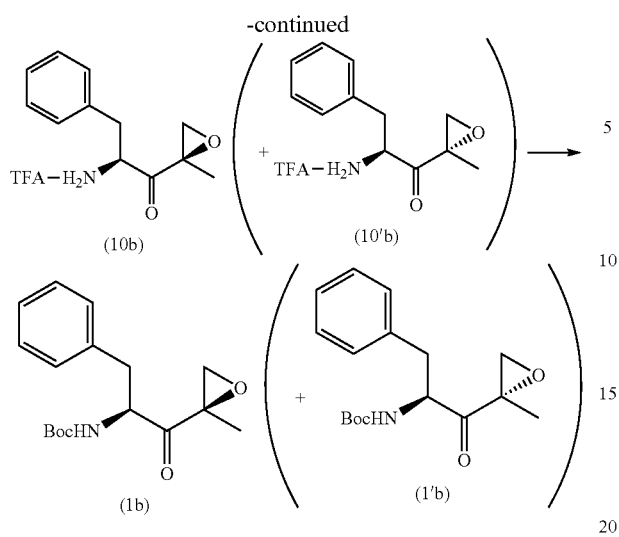

A solution of 1.0 g of a mixture of the compound (1b) and the compound (1'b) [(1b):(1'b)=26.4:1] in dichloromethane (4.0 g), was cooled to 10° C., and then, trifluoroacetic acid (1.9 g) was added. After completion of the addition, the reaction solution was stirred at 20° C. for 4 hours. After completion of the stirring, 1 μL of the reaction solution was injected to thin layer chromatography (TLC) and developed by means of a solvent of hexane:ethyl acetate=3:1, and by a color former of a phosphomolybdic acid solution, it was confirmed that all of the compounds (1b) and (1'b) as the starting material was reacted. After completion of the confirmation, at 25° C., methyl-tert-butyl ether (2.7 g) and n-heptane (18.8 g) were added to the reaction solution. After completion of the addition, the reaction solution was cooled to 0° C. and stirred for one hour. After completion of the stirring, crystals precipitated in the reaction solution were separated by filtration. The obtained crystals were washed with n-heptane (10 g) to obtain white crystals (951.0 mg) of a mixture of the compound (10b) and the compound (10'b) as a stereoisomer.

The obtained solution of a mixture (100.2 mg) of the compound (10b) and the compound (10'b) in dichloromethane (10 g) was cooled to 0° C., and then, triethylamine (119.2 mg) and then di-tert-butyl dicarbonate (130 mg) were added. After completion of the addition, the reaction solution was stirred at 20° C. for two hours. After completion of the stirring, by LC, it was confirmed that all of the compounds (10b) and (10'b) as the starting material was reacted. After completion of the confirmation, a dichloromethane solution of the compound (1b) (97.3 mg) was obtained.

The recovery from the mixture of the compound (1b) and the stereoisomer (1'b) was 92.2%, and the ratio of the compound (1b) to the compound (1'b) was improved to 39.0:1.

Further, in the analytical condition LC-3, the retention time (R.T.) and area value of the product after purification are as follows, and the retention time of the main product after purification agreed to the retention time of the compound (1b).

R.T. 27.9 min, 80.26%/compound (1b), 26.8 min, 2.06%/compound (1'b)

Here, the yield of the compound (1b) after purification was calculated by the quantitative analysis as described in Example 10.

The entire disclosures of Japanese Patent Application No. 2012-146821 filed on Jun. 29, 2012, Japanese Patent Application No. 2013-026801 filed on Feb. 14, 2013, U.S. Provisional Patent Application No. 61/735,196 filed on Dec. 10, 2012, and U.S. Provisional Patent Application No. 61/789,996 filed on Mar. 15, 2013 including specifications, claims and summaries are incorporated herein by reference in their entireties.

The invention claimed is:

1. A method for producing an alcohol compound of formula (3):

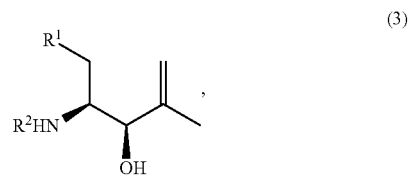

the method comprising reducing a compound of formula (2) in the presence of an amine borane complex of $R_3N \cdot BH_3$:

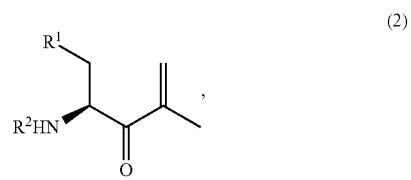

to form the alcohol compound of formula (3),
wherein:
$R^1$ is a hydrogen atom, a linear, branched or cyclic alkyl group, an optionally-substituted aromatic group, or an optionally-substituted heterocyclic group;
$R^2$ is a protective group for an amino group; and
each R of the amine borane complex of $R_3N \cdot BH_3$ is independently a hydrogen atom or a $C_{1-10}$ alkyl group, provided that at least one R is a $C_{1-10}$ alkyl group.

2. The method according to claim 1, wherein $R^1$ is an isopropyl group.

3. The method according to claim 1, wherein $R^1$ is a phenyl group.

4. The method according to claim 1, wherein $R^2$ is a t-butyloxycarbonyl group or a benzyloxycarbonyl group.

5. A method for producing an epoxyketone compound of formula (1):

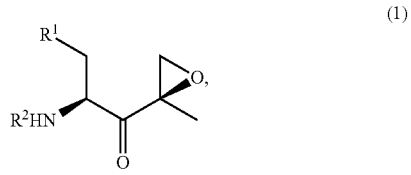

the method comprising oxidizing an alcohol compound of formula (4):

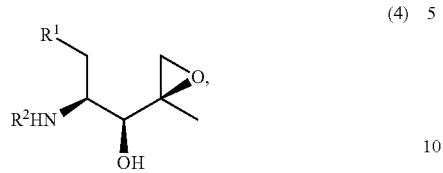

(4)

with an oxidizing agent in the presence of an N-hydroxy compound of formula (6):

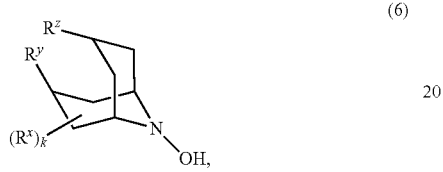

(6)

to form the epoxyketone compound of formula (1), wherein:

$R^1$ is a hydrogen atom, a linear, branched or cyclic alkyl group, an optionally-substituted aromatic group, or an optionally-substituted heterocyclic group;

$R^2$ is a protective group for an amino group;

$R^x$ is at least one substituent selected from the group consisting of a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a $(C_{1-12}$ alkyl)oxy group, a $(C_{3-12}$ cycloalkyl)oxy group, a $(C_{1-12}$ alkyl)thio group, a $(C_{3-12}$ cycloalkyl)thio group, a $(C_{1-12}$ alkyl)amino group, a $(C_{3-12}$ cycloalkyl)amino group, a di($C_{1-6}$ alkyl)amino group, a di($C_{3-6}$ cycloalkyl)amino group, a $C_{1-12}$ alkylcarbonyl group, a $C_{3-12}$ cycloalkylcarbonyl group, a $(C_{1-12}$ alkyl)oxycarbonyl group, a $(C_{3-12}$ cycloalkyl)oxycarbonyl group, a $(C_{1-12}$ alkyl)thiocarbonyl group, a $(C_{3-12}$ cycloalkyl) thiocarbonyl group, a $(C_{1-12}$ alkyl)aminocarbonyl group, a $(C_{3-12}$ cycloalkyl)aminocarbonyl group, a di($C_{1-6}$ alkyl) aminocarbonyl group, a di($C_{3-6}$ cycloalkyl)aminocarbonyl group, a $(C_{1-12}$ alkyl)carbonyloxy group, a $(C_{3-12}$ cycloalkyl) carbonyloxy group, a $(C_{1-12}$ alkyl) carbonylthio group, a $(C_{3-12}$ cycloalkyl) carbonylthio group, a $(C_{1-12}$ alkyl)carbonylamino group, a $(C_{3-12}$ cycloalkyl) carbonylamino group, a di($C_{1-12}$ alkylcarbonyl)amino group, a di($C_{3-12}$ cycloalkylcarbonyl) amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocyclo alkenyl group, a $C_{2-6}$ alkynyl group, a $C_{2-6}$ haloalkynyl group, a benzyl group which optionally is substituted by $R^a$, a benzyloxy group which optionally is substituted by $R^a$, a benzylthio group which optionally is substituted by $R^a$, a benzylamino group which optionally is substituted by $R^a$, a dibenzylamino group which optionally is substituted by $R^a$, a benzylcarbonyl group which optionally is substituted by $R^a$, a benzyloxycarbonyl group which optionally is substituted by $R^a$, a benzylthiocarbonyl group which optionally is substituted by $R^a$, a benzylaminocarbonyl group which optionally is substituted by $R^a$, a dibenzylaminocarbonyl group which optionally is substituted by $R^a$, a benzylcarbonyloxy group which optionally is substituted by $R^a$, a benzylcarbonylthio group which optionally is substituted by $R^a$, a benzylcarbonylamino group which optionally is substituted by $R^a$, a di(benzylcarbonyl)amino group which optionally is substituted by $R^a$, an aryl group which optionally is substituted by $R^a$, an aryloxy group which optionally is substituted by $R^a$, an arylthio group which optionally is substituted by $R^a$, an arylamino group which optionally is substituted by $R^a$, a diarylamino group which optionally is substituted by $R^a$, an arylcarbonyl group which optionally is substituted by $R^a$, an aryloxycarbonyl group which optionally is substituted by $R^a$, an arylthiocarbonyl group which optionally is substituted by $R^a$, an arylaminocarbonyl group which optionally is substituted by $R^a$, a diarylaminocarbonyl group which optionally is substituted by $R^a$, an arylcarbonyloxy group which optionally is substituted by $R^a$, an arylcarbonylthio group which optionally is substituted by $R^a$, an arylcarbonylamino group which optionally is substituted by $R^a$, and a di(arylcarbonyl)amino group which optionally is substituted by $R^a$;

k is an integer of from 0 to 12 and when k is two or more, each $R^x$ is the same or different;

each $R^y$ and each $R^z$ is independently a hydrogen atom or $R^x$, or $R^y$ and $R^z$ together form methylene which optionally is substituted by one $R^x$ or two $R^x$s which are the same or different; and $R^a$ is halogen, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkyl sulfonyl group, a $C_{1-6}$ haloalkylsulfenyl group, a $C_{1-6}$ haloalkylsulfinyl group, a $C_{1-6}$ halo alkylsulfonyl group, a $C_{2-6}$ alkenyl group, a $C_{2-6}$ haloalkenyl group, a $C_{2-6}$ alkenyloxy group, a $C_{2-6}$ halo alkenyloxy group, a $C_{2-6}$ alkenylsulfenyl group, a $C_{2-6}$ alkenylsulfinyl group, a $C_{2-6}$ alkenyl sulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_2$-$C_6$ haloalkynylsulfonyl group, $NO_2$, CN, a formyl group, OH, SH, $NH_2$, SCN, a $C_{1-6}$ alkoxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di-$C_{1-6}$ alkylamino group, the number of $R^a$ to be substituted, is from 1 to 5, and when $R^a$ is two or more, each substituent is the same or different.

6. The method according to claim 5, wherein $R^1$ is an isopropyl group.

7. The method according to claim 5, wherein $R^1$ is a phenyl group.

8. The method according to claim 5, wherein $R^2$ is a t-butyloxycarbonyl group or a benzyloxycarbonyl group.

9. An epoxy alcohol compound of formula (7):

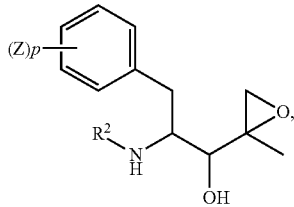

(7)

wherein:

$R^2$ is —C(O)$OR^b$;

$R^b$ is a $C_{1-6}$ alkyl group;

Z is a halogen atom, a nitro group, a cyano group, a $C_{1-6}$ alkyl group or a $C_{1-6}$ haloalkyl group; and p is an integer of 0, 1, 2, 3, 4 or 5.

10. The method of claim 1, wherein $R^1$ is a hydrogen atom, a linear, branched or cyclic alkyl group, or an optionally-substituted aromatic group.

11. The method of claim 5, wherein $R^1$ is a hydrogen atom, a linear, branched or cyclic alkyl group, or an optionally-substituted aromatic group.

12. The method of claim 1, wherein the amine borane complex is a complex of $R_2NH.BH_3$, in which each R is independently a $C_{1-10}$ alkyl group.

13. The method of claim 1, wherein the amine borane complex is selected from the group consisting of dicyclohexylamine-$BH_3$, cyclohexyl-isopropylamine-$BH_3$, tert-butylamine-$BH_3$, diisopropylamine-$BH_3$, cyclohexyl-methylamine-$BH_3$, diisoamylamine-$BH_3$, tert-butyl-methylamine-$BH_3$, (S)-phenylethylamine-$BH_3$, (R)-phenylethylamine-$BH_3$, cyclohexylamine-$BH_3$ and cyclopentylamine-$BH_3$.

14. The method of claim 1, wherein the amine borane complex is selected from the group consisting of dicyclohexylamine-$BH_3$, diisopropylamine-$BH_3$ and di-sec-butylamine-$BH_3$.

* * * * *